United States Patent [19]

Utrata

[11] Patent Number: 4,642,090
[45] Date of Patent: Feb. 10, 1987

[54] DISPOSABLE COMBINATION SCALPEL BLADE AND INCISION IRRIGATOR FOR OPHTHALMOLOGICAL USE

[76] Inventor: Peter J. Utrata, 2680 Sandover Rd., Columbus, Ohio 43220

[21] Appl. No.: 708,137

[22] Filed: Mar. 4, 1985

[51] Int. Cl.⁴ .............................................. A61B 17/20
[52] U.S. Cl. ...................................... 604/22; 128/305
[58] Field of Search ............................ 128/305, 305.1; 30/123.3; 604/22; 433/30, 31

[56] References Cited

U.S. PATENT DOCUMENTS

| | | | |
|---|---|---|---|
| 878,524 | 2/1908 | Gregory | 128/305 |
| 1,390,720 | 9/1921 | Powers | 128/305 |
| 2,984,009 | 5/1961 | Codoni | 433/30 |
| 4,136,700 | 1/1979 | Broadwin et al. | 128/305 |

Primary Examiner—Dalton L. Truluck
Assistant Examiner—Mario Costantino
Attorney, Agent, or Firm—John L. Gray

[57] ABSTRACT

A disposable irrigating combination scalpel blade and incision irrigator provided with a hollow scalpel handle from which extends the scalpel blade and a cannula connected to the interior of the hollow blade handle and positioned within a critical angular range to the cutting edge of the scalpel so as to permit continuous washing away of blood during the surgical procedure. A flow of fluid to the cannula through the hollow scalpel handle is controlled by a foot pedal operated by the surgeon leaving one hand free for manipulation of the scalpel blade and the other hand free to hold other instruments such as forceps used in the surgical procedures.

7 Claims, 6 Drawing Figures

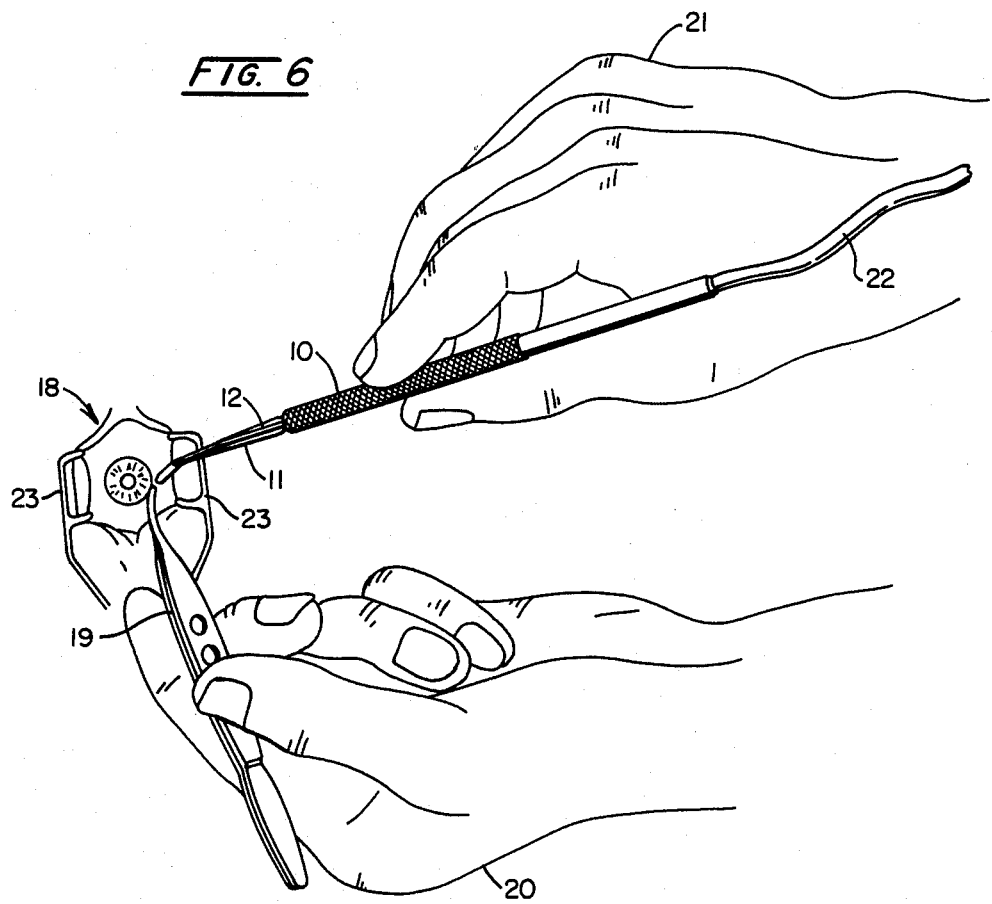

DISPOSABLE COMBINATION SCALPEL BLADE AND INCISION IRRIGATOR FOR OPHTHALMOLOGICAL USE

BACKGROUND OF THE INVENTION

In my copending patent application, Ser. No. 599,133, entitled "A Combination Scalpel Blade and Incision Irrigator for Ophthalmological use," there is disclosed such a device which involves supporting a cannula so that it may be attached to a conventional scalpel blade to form an acute angle with said scalpel blade so as to permit the washing away of blood and other fluids during surgery.

The trend in modern ophthalmic surgery is to make incisions more posterially away from the bloodless cornea into the sclera. The sclera contains significant blood vessels. The flow of blood from these vessels can prevent the surgeon from observing that portion of the eye in which he wishes to make an incision. The result has been a need for irrigation for these newer surgical methods. This is a problem which is faced not only in the two-step cataract surgical incision, which is done in the sclera, but also is applicable in the large scleral flaps made by surgeons specializing in glaucoma surgery while doing a posterior lip sclerectomy. There also is a need for continuing blood removal controllable by the surgeon in scleral dissections done by surgeons conducting retinal procedures.

This type of surgery is extremely delicate. It is conducted under an operating power microscope and the current state of the art requires the surgeon to direct an assistant to spray sterile saline on the area where the blood is obscuring the surgeon's vision. Considering the space limitations and the extremely delicate nature of the surgery, this is a very unsatisfactory procedure.

SUMMARY OF THE INVENTION

The present invention involves a disposable combination scalpel blade and incision irrigator positioned at one end of a hollow scalpel handle. The other end of the hollow scalpel handle is adapted to receive the male portion of a hose for the flow of fluid through the scalpel blade handle and through the cannula. The cannula is positioned so that the flow of fluid from the cannula will wash away the blood from the eye in the area where the scalpel blade is being used to make an incision and is so positioned on the scalpel blade that the scalpel barrel may be rotated by the surgeon in the normal fashion in order to perform the particular surgical procedure desired. The scalpel blade may be completely rotated. By use of the foot pedal to control the flow of fluid through the cannula, the other hand of the surgeon is free to utilize other instruments, such as forceps, in connection with the surgical procedure being conducted.

In one embodiment of the invention, the entire combination scalpel blade, incision irrigator, and hollow scalpel handle is disposable. The handle is made of plastic. Because the "heft" of an instrument is important to the surgeon in this sort of delicate surgery and because many surgeons are used to working with a metal scalpel, another embodiment of the invention involves the use of a conventional metal scalpel handle onto which the disposable plastic scalpel blade and cannula containing portion may be attached, such as by a threaded connection.

It is therefore an object of this invention to provide a disposable combination scalpel blade and irrigating cannula to enable blood and debris to be cleared from the eye while making an incision into the sclera of the human eye.

It is another object of this invention to provide such an instrument wherein the angular relationship of the cannula to the scalpel blade and the spacing of the tip of the cannula from the end of the scalpel blade will permit the scalpel blade to be used in its normal fashion and rotated, if necessary.

It is still another object of this invention to provide a disposable combination scalpel blade and irrigating cannula wherein the flow of fluid to the cannula is controlled by means of a foot pedal.

These, together with other objects and advantages of the invention, should become apparent in the details of construction and operation, as more fully described herein and claimed, reference being had to the accompanying drawings forming a part hereof wherein like numerals refer to like parts throughout.

BRIEF DESCRIPTION OF THE DRAWINGS

FIG. 6 is a perspective view of the combination scalpel blade and irrigating cannula being used to make an incision into the sclera of the human eye showing that both hands of the surgeon are free to use the scalpel and forceps while the surgeon controls the flow of fluid by a foot pedal.

DETAILED DESCRIPTION OF THE INVENTION

Figure 1:
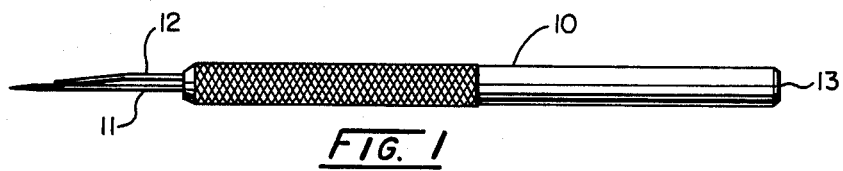
FIG. 1 is a side elevation view of the disposable combination scalpel blade and irrigating cannula.

Referring now more particularly to FIG. 1, hollow handle 10 is provided with a scalpel blade 11 and a cannula 12 extending from one end of hollow handle 10, the hollow cannula 12 being connected to the hollow interior of the blade handle 10. This will become more apparent from an examination of FIG. 3, discussed infra. The cannula 12 is spaced from the end of the scalpel blade 11, preferably approximately 9 mm so as not to interfere with the normal surgican procedures performed by the surgeon in using the instrument. The angular displacement from the scalpel blade 11 of the cannula 12 may vary from 0° to approximately 6°. Any wider angular displacement would result in a handle which would have too large a diameter to comfortably fit the surgeon's hand. The flow of fluid from the cannula 12 performs two functions. It not only washes away the blood and debris from the cutting area, but also continuously washes the end of the scalpel blade 11 so that the surgeon has good visual identification of the edge of the blade. Open end 13 of the hollow handle 10 is adapted to receive a conventional male fitting on a tube connected to a source of sterile saline through a conventional valve (not shown) controlled by a conventional foot pedal (not shown). This tube connected to the hollow handle can be seen in FIG. 6.

Figure 2:
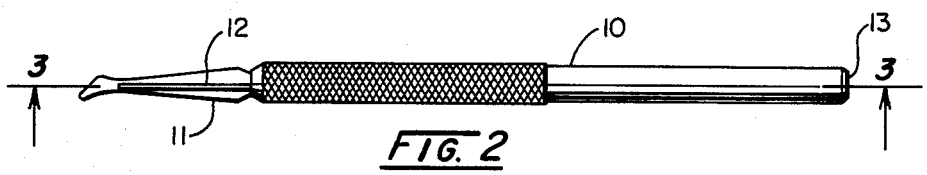
FIG. 2 is a plan view of the device shown in FIG. 1.

Referring now more particularly to FIG. 2, the relationship of the cannula 12 to the scalpel blade 11 is shown with the scalpel blade being essentially centrally disposed in the end of the handle 10 and the cannula 12, also centrally disposed, but its position varying from lying adjacent to the scalpel blade 11 to being spaced to the outer periphery of the scalpel blade handle 10.

Figure 3:
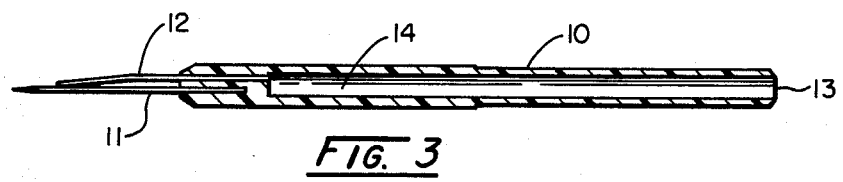
FIG. 3 is a section of the device shown in FIG. 2 on the section 3—3.

Referring now more particularly to FIG. 3, it will be seen that the cannula 12 is connected to the interior hollow portion 14 of hollow handle 10 so that the cannula 12 is thus connected through the hollow portion 14 to the saline hose which is inserted into the open end 13 of the scalpel handle 10.

Figure 4:
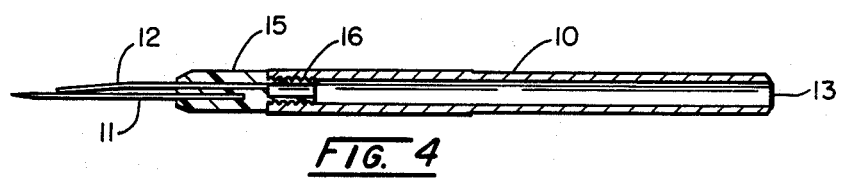
FIG. 4 is a section of another embodiment of the device shown in FIG. 2 wherein the scalpel handle is threadedly connected to the disposable portion of the scalpel blade handle containing the scalpel blade and irrigating cannula.

In FIG. 4, the scalpel handle 10 is preferably made of a metal, whereas the portion of the scalpel handle 15, which has the scalpel blade and the cannula fixedly contained therein, is made from a plastic material but is threadedly connected, as shown at 16, to the interior of the scalpel handle 10 thus enabling the portion 15 to be disposed of following use and the metal portion 10 to be retained by the surgeon and following proper sterilization, to be reused.

Figure 5:
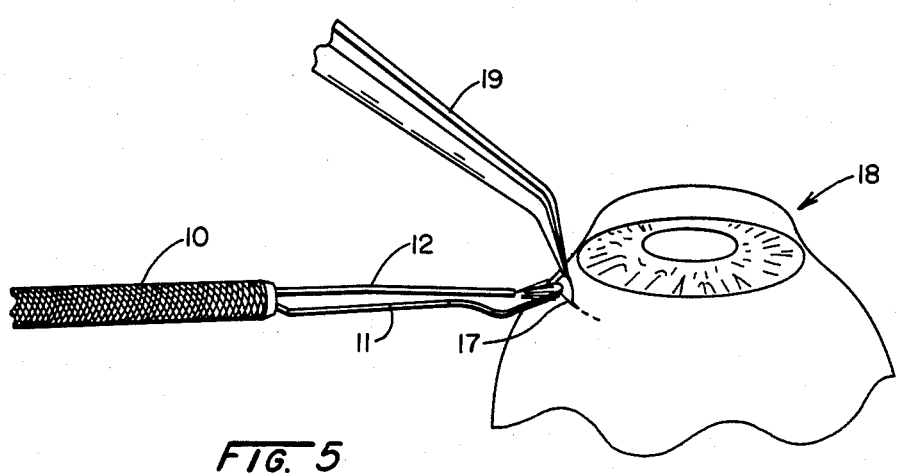
FIG. 5 is a perspective view of the combination scalpel blade and irrigating cannula being used to make an incision into the sclera of the human eye.

Referring now more particularly to FIG. 5, the scalpel blade 11 and the irrigating cannula 12 are shown in use in making an incision in the sclera 17 of the human eye, shown generally at 18. Forceps 19 may be used to lift up the flap of the sclera produced from the incision made with scalpel blade 11.

Referring now more particularly to FIG. 6, the advantage of the use of the scalpel blade 11 and the irrigating cannula 12 will be more readily apparent wherein it is shown that one of the surgeon's hands 20 can be used to hold the forceps 19 while the other surgeon's hand 21 can be holding the scalpel blade handle 10 and operating it in a normal fashion. By using the foot pedal, the surgeon is able to control the fluid flow through the tube 22 and through the hollow handle 10 into the cannula 12 so that it is directed to the end of the scalpel blade 11 so as to wash away the blood and debris from the incision being made and to provide the surgeon with a clear view of the area in which he wishes to make the incision. In this case spacers 23—23 are used in the conventional fashion to hold the eyelids back to permit the surgeon to have ready access to the eye shown generally at 18.

By means of this device, the available infusion is positioned exactly when and where the surgeon desires it and is controlled by the surgeon. In addition to using the scalpel blade 11 and irrigating cannula 12 for the purposes described, the cannula 12 may also be used to keep the cornea wet.

While the angular relationship between the end of the cannula 12 adjacent the scalpel blade 11 and the scalpel blade 11 can vary, it is preferred that the angle be between 0° and 6° and a preferred angle is approximately 4°. It is preferred that the end of the irrigating cannula 12 be positioned far enough from the cutting edge of the scalpel blade 11 so that it does not interfere with that function and permits rotation of the scalpel blade 11 as needed. Normally this positions the end of the cannula 12 about at the heel of the scalpel blade 11 cutting edge or about 9 mm from the end of the scalpel blade 11.

While this invention has been described in its preferred embodiment, it is appreciated that variations thereon may be made without departing from the true scope and spirit of the invention.

What is claimed is:

1. A disposable combination scalpel handle blade and an incision irrigator for ophthalmological use comprising:

a hollow scalpel handle closed at one end and open at the other end, said open end being adapted to receive and frictionally hold a flexible tube, said closed end having a scalpel blade provided with a cutting edge thereon and fixedly secured in the closed end of said scalpel handle and extending outwardly from said closed end and approximately coaxial therewith, said closed end of said scalpel handle also having a cannula, fixedly secured therein and extending from said closed end of said handle and disposed parallel to said scalpel blade at said closed end at an angle so that fluid flowing through said cannula will impinge only upon the cutting edge of said scalpel blade, and said cannula being fluidwise connected to the interior of said hollow scalpel handle, whereby blood and debris from the incision being made by the cutting edge of said scalpel blade is washed away and the fluid does not obscure the surgeon's view so that the surgeon will have a clear view of the area in which he wishes to extend his incision.

2. The device of claim 1 wherein the end of said cannula extending from said closed end of said handle forms an acute angle with said scalpel blade.

3. The device of claim 2 wherein said acute angle is between 0° and 6°.

4. The device of claim 2 wherein said acute angle is approximately 4°.

5. The combination scalpel blade and incision irrigator of claim 1 wherein said scalpel handle comprises two parts, said first part comprising a holow interior, and said second part having a scalpel blade fixedly secured therein, said first and second parts being detachably secured together.

6. The device of claim 5 wherein said first part of said scalpel handle is made of metal and said second part of said scalpel handle is made of plastic.

7. The device of claim 6 wherein said first and second parts of said scalpel handle are threadedly connected.

* * * * *